United States Patent [19]

Marsoner et al.

[11] 4,446,872

[45] May 8, 1984

[54] METHOD AND APPARATUS FOR DETERMINING SYSTOLIC TIME INTERVALS

[75] Inventors: Hermann J. Marsoner; Günther Savora, both of Graz, Austria

[73] Assignee: AVL AG, Schaffhausen, Switzerland

[21] Appl. No.: 937,886

[22] Filed: Aug. 29, 1978

[30]  Foreign Application Priority Data

Sep. 8, 1977 [CH]  Switzerland ..................... 11030/77

[51] Int. Cl.³ .............................................. A61B 5/04
[52] U.S. Cl. ..................................... 128/700; 128/715
[58] Field of Search .............................. 128/695–706, 128/687–688, 715

[56] References Cited

U.S. PATENT DOCUMENTS

| | | | |
|---|---|---|---|
| 3,318,303 | 5/1967 | Hammacher | 128/687 |
| 3,543,050 | 11/1970 | Paine | 128/696 |
| 3,773,033 | 11/1973 | Rodbard et al. | 128/687 |
| 3,878,832 | 4/1975 | Tickner et al. | 128/696 |
| 3,878,833 | 4/1975 | Arneson et al. | 128/672 |
| 3,965,339 | 6/1976 | Mount et al. | 128/695 |
| 4,023,563 | 5/1977 | Reynolds et al. | 128/672 |

OTHER PUBLICATIONS

Lewis, R. P. et al., "Systolic Time Intervals", in No-n-Invasive Cardiology by A. M. Weissler, M.D., Grune & Stratton, Publ. N.Y. & London, 1974, pp. 301–368.
Wayne, Howard H., "Non-Invasive Technics in Cardiology", Yrbk Publ., Chicago 1973, pp. 6–7.
Wandermanne, K. et al., "LV Performance in Mitral Regurgitation Assessed With Systolic Time Intervals and Echocardiography", Amer. Jrnl. Cardiology, Dec. 1976, vol. 38, pp. 831–835.

Primary Examiner—Kyle L. Howell
Assistant Examiner—Francis J. Jaworski
Attorney, Agent, or Firm—Ladas & Parry

[57]  ABSTRACT

A method and apparatus for determining the systolic time intervals from the electrocardiogram (ECG) wherein initially there is detected at least the point in time of the Q-wave in the ECG. Thereafter there is determined the time point for the start of the second cardiac sound and then there is determined the start of the ascent of the pulse curve as well as the position as a function of time of the dicrotic depression. Then there is checked the timewise correlation of the signals with respect to one another, and finally, there is checked whether the timewise spacing of characteristic points of the signals are within predetermined tolerances. The apparatus for performance of the method contains analogue signal processing means for ECG-signals, analogue signal processing means for cardiac sound signals, analogue signal processing means with which there is operatively associated a computer and output device.

5 Claims, 11 Drawing Figures

METHOD AND APPARATUS FOR DETERMINING SYSTOLIC TIME INTERVALS

BACKGROUND OF THE INVENTION

The present invention relates to a new and improved method of, and apparatus for, determining the systolic time intervals from the electrocardiogram, the heart or cardiac signal and the pulse curve, these time intervals, after forming their mean or average value, constituting the basis for determining the functional state of the myocardium.

Measurement of the functional state of the myocardium previously was associated with appreciable clinical difficulties. The usual characteristics of the cardiac output, i.e., the minute output of the heart, the blood pressure, the pulse frequency and the ECG, individually did not provide any or only insufficient information concerning the contraction force of the heart and its reserve. Frequently however there is required a parameter which enables analysis as to whether the heart is loaded to the limits of its output capability or still has a functional reserve. Such parameter should also enable analysis or diagnosis whether and to what degree therapeutic intervention would be beneficial.

As one such type of parameter for the activity of the contracting elements of the heart muscle there was employed the nature of the isometric contraction of the myocardium. This was done because the development of the isometric contraction, i.e, the contraction of the heart muscle during constant volume content of the heart chambers, essentially is governed by the voltage-velocity characteristics of the contractable elements. This process is most effectively characterized by the first time differential quotient of the pressure course at the left heart chamber. The maximum of this first time differential quotient of the left chamber pressure previously was viewed as the most effective parameter for examining the functional state of the myocardium. This characteristic is sensitive enough to detect the increase of the contraction force of the healthy myocardium by administering digitalis. To determine the first time differential quotient from the pressure course in the left heart chamber it is however necessary to introduce a catheter pressure transmitter into the left heart. Such type of left-intracardiac catheter examinations are reserved for special cardiology laboratories. Such examinations are of course associated with the well known dangers for the patient, and additionally, they cannot be repeatedly employed for therapy or for controlling the effects of a therapeutic intervention.

Figure 1:
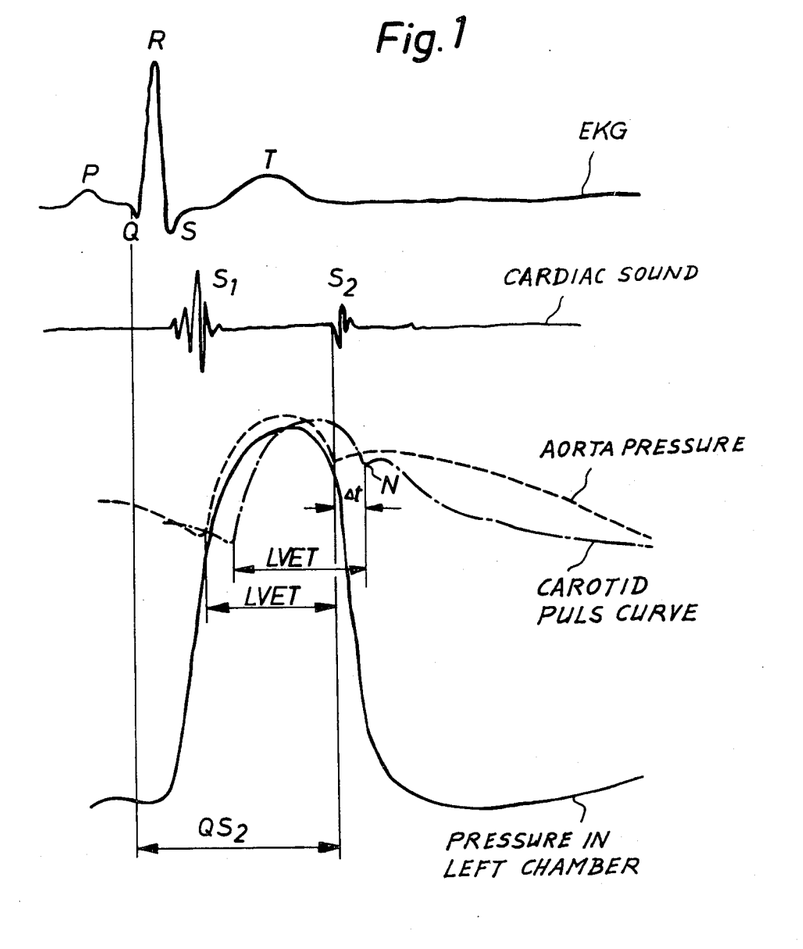
FIG. 1 illustrates a part of the ECG-curve, a cardiac sound curve as well as the curves which represent the pressure course in the left heart chamber, in the aorta and in the carotid.

Therefore, there is prevalent the demand for a non-operative method for measuring the functional state of the myocardium, which can be repeatedly carried out as often as desired without any danger for the patient. This method is predicated upon the determination of the so-called systolic time intervals of the heart beat cycle. The total electro-mechanical systole, in other words that part of the cardiac action period, beginning with the excitation of the heart chambers (FIG. 1) and terminating with the closure of the aortic valve following completed expulsion of the blood into the aorta, is divided into two partial periods. The first partial period, the so-called presphygmic phase or period, hereinafter also referred to as the pre-ejection period or briefly PEP, extends from the beginning of the electrical excitation of the heart chambers, which can be determined from the start of the Q-wave (FIG. 1) of the ECG, until opening of the aortic valve. This is the time duration of the isometric contraction of the heart. During this period, with filled ventricle, there is built-up in the heart that pressure which is needed in order to eject the chamber or ventricle content out of the ventricle against the force of the arterial system. Only then is the aortic valve opened.

Already the pre-ejection time or PEP constitutes a measure for the contraction capability of the myocardium. Short preejection times and rapid pressure build-up can be generally considered as a sign of a high myocardium contraction force, whereas a weakened myocardium requires for the pressure build-up a comparatively longer time span.

Following the contraction of the heart muscle and the pressure build-up in the left heart chamber is the ejection period, whose time duration is referred to as the ejection time, also the left ventricular ejection time, or briefly LVET. The ejection time or LVET begins with the slope ascent of the pulse pressure curve and terminates with the so-called dicrotic depression N (see FIG. 1).

The ejection time or LVET thus begins at the moment of opening of the aortic valve and terminates conjointly with the end of the total electro-mechanical systole upon closure of the aortic valve. The moment of the aortic valve opening can not be readily directly determined without any operation. It is however true that it is possible to determine the ejection time or LVET from the arterial pressure course. This can be done not only from the central pressure pulse but also from the peripheral pressure pulse which is derived approximately at the carotid surface. The peripheral pressure course is shifted by the phase travel time $\Delta t$ of the pulse wave between the aorta and the removal location at the carotid, but the thus determined ejection time is however representative. The correlation between the non-operative and the operatively determined ejection times or LVET's is almost ideal with a correlation quotient $R = 0.99$.

Qualitatively it can be easily seen that a myocardium function can be designated as good when a short contraction time with rapid pressure build-up precedes a long lasting and thorough ejection period or time. With reduced myocardium contraction capability a prolonged contraction time or period is followed by a shortened weak ejection time or period. In fact, the relationship or ratio of the contraction time and ejection time, i.e. PEP/LVET constitutes a very sensitive parameter of the myocardium contractability independent of the heart or cardiac frequency, as will be apparent from relevant scientific publications in this field which are extremely closely correlated to the operative measured parameters of the myocardium contractability.

Both the contraction time or PEP as well as also the ejection time or LVET are, as stated, measures for the myocardium function. However they are, at least up to a certain degree frequency-dependent, as this will be apparent from the book entitled "Non-Invasive Cardiology" of Arnold M. Weissler. The experiments of Weissler, which have been completely confirmed by the hereinafter cited literature, demonstrated that in a pulse frequency range of 60 to 120 beats per minute a linear correlation prevails between the pulse frequency and the normal values of PEP and LVET. Furthermore, from such studies it has been found that the ratio of PEP/LVET constitutes a quotient which is independent of the pulse frequency, the normal value of which is at 0.35 and constitutes an extremely sensitive measure for the functional state of the myocardium. From this there can be easily qualitatively determined that such quotient immediately images any prolongation of the contraction phase or PEP in relation to the ejection phase or LVET. A prolongation of the contraction time or PEP in relation to the ejection or LVET corresponds to a poor functional state of the myocardium and an increased quotient K=PEP/LVET.

That this quotient K formed from PEP and LVET constitutes an exceptionally reliable and sensitive measure for the myocardium function has already been proven in numerous scientific works. It correlates in all respects with the dp/dt-values and enables the direct comparison of patients having different pulse frequencies.

To determine the contraction time or PEP and the ejection time or LVET there is required a derivation of ECG, whose Q-wave indicates the start of the electro-mechanical systole, further a heart sound derivation, from which there can be derived the start of the second heart or cardiac sound $S_2$, which signals the end of the electro-mechanical systole $QS_2$. The start and end of the ejection time or LVET is best obtained from a pulse curve derived at the surface of the carotid.

All three signals can be obtained without any operation and quickly from the body of the patient. Thus there is fulfilled the most important prerequisite which has been placed upon the present method. Examination is accomplished without any danger to or strain upon the patient and can be repeatedly carried out as often as desired.

By recording the above-mentioned signals, ECG, heart or cardiac sound, carotid pulse curve, it is possible to measure the systolic time intervals. Experience has shown that for determining the quotient K=PEP/LVET there must be evaluated at least ten pulse beats and there must be determined their systolic time intervals, in order that there can be ascertained with adequate accuracy the quotient K. This time-consuming evaluation of the recorded curves, which must be performed by a skilled individual and the subsequent formation of the mean value, constituted however an appreciable limitation of the usability of this technique. Additionally, with extremely large variations of the shape of the signals, which can be quite different from patient to patient, there arise subjective errors, so that tests by various individuals on the same patients could lead to completely different results and diagnoses. Furthermore, the time-consuming manual evaluation of the recorded curves does not allow for any progress control over a longer time as well as any real time monitoring of the myocardium function.

SUMMARY OF THE INVENTION

Hence, with the foregoing in mind the present invention is concerned with the object of providing an improved method and apparatus by means of which there can be detected characteristic moments with the aid of signals, derived from the body of a patient of the ECG, the cardiac sound and the pulse pressure curve and wherein there can be accomplished an automatic evaluation of such signals.

Now in order to implement this and still further objects of the invention, which will become more readily apparent from the foregoing description and the detailed description to follow, the inventive method is manifested by the features that there is determined in the electrocardiogram at least the time point of the Q-wave, there is determined the point in time of the start of the second heart or cardiac sound, there is determined the start of the ascent of the pulse curve as well as the timewise position of the dicrotic depression, and that there is accomplished a checking of the timewise correlation of the signals with respect to one another, and that there is checked whether the spacing as a function of time of characteristic points of the signals lies within predetermined tolerances.

The apparatus for the performance of the aforementioned method aspects is manifested by the features that it contains the following structure:

analogue signal processing means for ECG;

analogue signal processing means for heart or cardiac sounds;

analogue signal processing means for pulse pressure curves; and process control means with which there is operatively correlated a computer and output device.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

As will be apparent from the previous comments, in order to fulfill the strived for objectives, there must be determined the following points in time during the course of the signals which are tapped-off of the body of the patient;

(1) The point in time or time of start of the Q-wave in the ECG, which indicates the start of the electro-mechanical systole.

(2) The start of the second cardiac or heart sound $S_2$ which signals the closure of the aortic valve.

(3) The start of the slope ascent of the pulse pressure curve.

(4) The minimum course of the dicrotic depression in the pulse pressure curve.

Initially there will be explained more fully that part 9 of the apparatus of the present development which is suitable for examination of the electrocardiogram (hereinafter briefly referred to sometimes as EKG or ECG), in order to determine the point in time of the start of the Q-wave in the ECG.

Figures 2, 3:
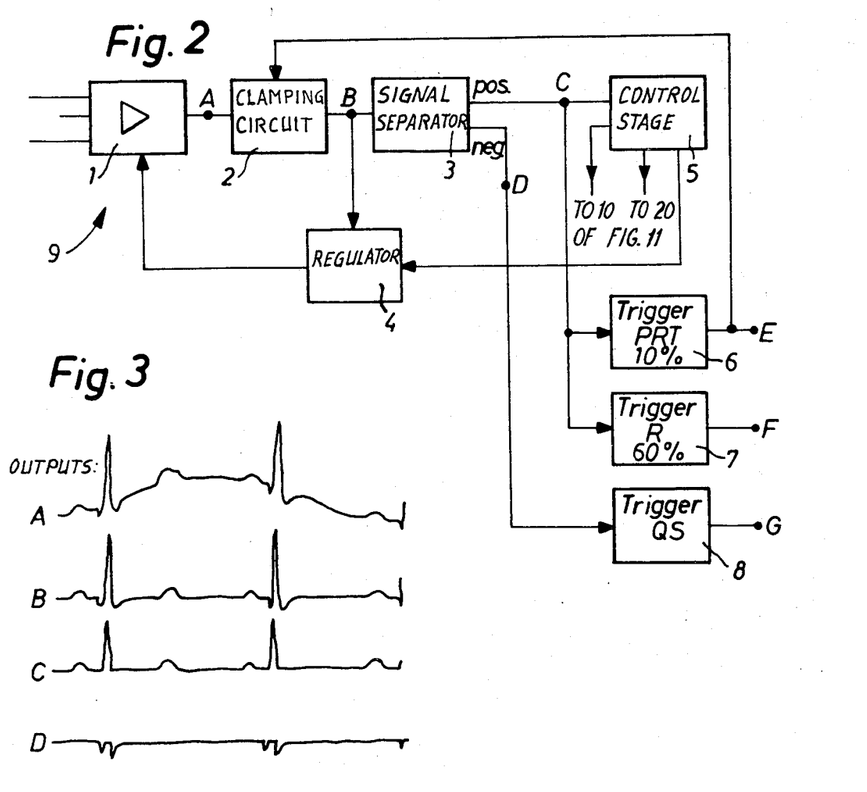
FIG. 2 is a block circuit diagram showing processing of the ECG-signal.
FIG. 3 illustrates the shape of the signals which appear at the individual blocks of the circuitry of FIG. 2.

The construction of such part 9 which is suitable for the analogue processing of the ECG-signal will be apparent from the block circuit diagram of FIG. 2. A high-ohmic differential amplifier 1, the gain of which can be electronically controlled, is connected by means of standard ECG-electrodes (not shown) with the patient. At the point A at the output of the amplifier 1 there appears the ECG-signal in the form of a low-ohm electrical signal. Usually there is superimposed upon this signal very low-frequency voltage fluctuations and additionally also a direct-current voltage, as shown by the curve A of FIG. 3.

Figure 4:
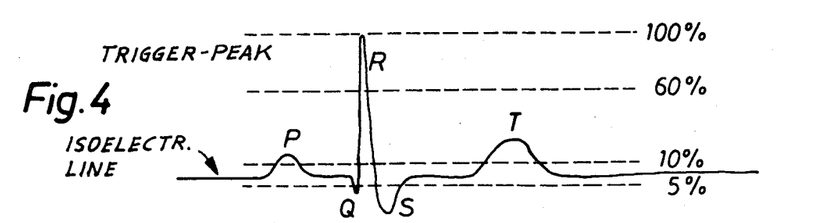
FIG. 4 illustrates part of the ECG-signal which is placed into correlation with the peaks of the individual trigger stages of this circuitry of FIG. 2.

The stage 2 following the differential amplifier 1 has the function of eliminating the low-frequency fluctuations and the direct-current voltage components in a manner such that the isoelectric line (FIG. 4) in the ECG, i.e. the null line of the curve B of FIG. 3 coincides with the electrical null potential of the entire circuitry. This clamping circuit 2 is formed by a highpass filter, where there are not used the positive amplitudes, or only in an extremely attenuated state, for formation of the mean or average value. The threshold frequency of this highpass filter 2 is in the order of about 0.3 Hz.

The output signal B from the clamping circuit or stage 2 is delivered both to a signal separator 3 and to a regulator or controller 4. The signal separator 3 separates the positive and negative components of the ECG-signal in relation to the isoelectric line or the null potential of the circuit. At the one output C of the signal separator 3 there appear the positive signal components (curve C of FIG. 3) of the ECG-signal, i.e., the waves P, R and T and at the other output D of the separator 3 there appear the negative signal components (curve D of FIG. 3), i.e., the waves Q and S. The regulator 4 is controlled by a control stage 5 in a manner such that in each instance during one period, which lasts approximately 250 milliseconds after the occurrence of the R-wave in the ECG, the gain of the preamplifier 1 is effected such that the R-wave of the ECG-signal at the output B always corresponds to a predetermined peak value.

Figure 5:
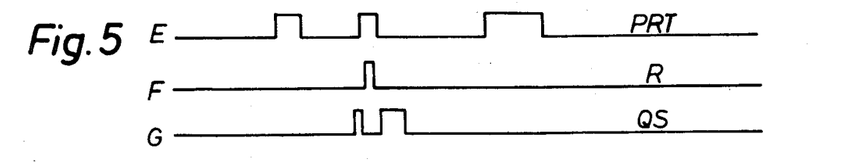
FIG. 5 are graphs illustrating the pulse shapes at the outputs of the trigger stages of FIG. 2.

At the outputs of the signal separator 3 there are derived by trigger stages 6, 7 and 8 pulse-like signals, as best seen by referring to FIG. 5. The first trigger stage 6, the trigger peak of which is preferably set at 10 percent (FIG. 4) of the peak amplitude of the R-wave, delivers pulse-shaped signals (curve E of FIG. 5) which characterize the appearance of the P, R and T-waves of the ECG. The second trigger stage 7, the trigger peak of which is preferably set at 60 percent (FIG. 4) of the peak amplitude of the R-wave, delivers a pulse-shaped signal (curve F of FIG. 5) which for itself indicates the appearance of the R-wave. Since the T-wave of the ECG also can reach extremely high amplitudes, by R-C combinations there is insured that R-wave and T-wave cannot be confused. There is thus accomplished both an amplitude discrimination as well also a frequency discrimination, since the T-wave in the ECG is always a clear oscillation of lower frequency than the R-wave. The third trigger stage 8, controlled by the negative signal components of the signal separator 3, delivers pulse-shaped signals (curve G of FIG. 5) which characterize the presence of the Q-wave and S-wave, respectively, (FIG. 4) of the ECG.

Figure 6:
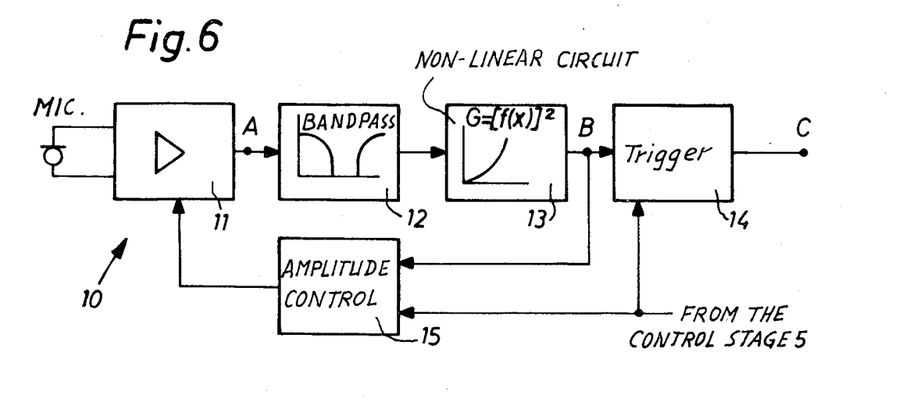
FIG. 6 is a block circuit diagram suitable for processing the cardiac or heart sound signals.
Figure 7:
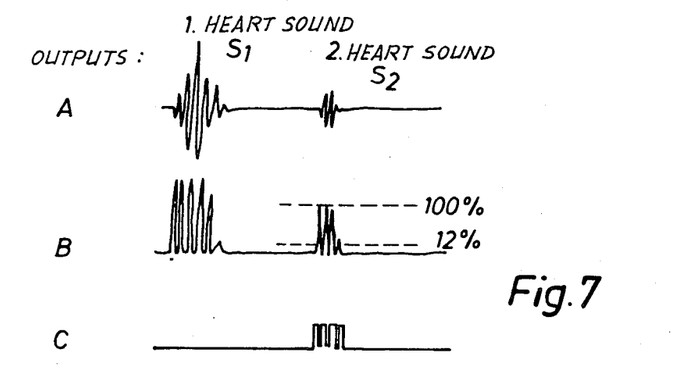
FIG. 7 are curves showing the manner in which the first and second heart sound signals or heart sounds are processed in the circuitry of FIG. 6.

The construction of the part or means 10 for the analogue signal processing of the cardiac or heart wave (curve A of FIG. 7) will be apparent from the block circuit diagram of FIG. 6. A pre-amplifier 11, the gain of which can be regulated, is operatively connected with a microphone Mic serving for the pick-up of the heart sound signals. A bandpass 12 connected in circuit at the output side of the pre-amplifier 11 limits the frequency band of the cardiac sound signal. The thus filtered cardiac or heart sound signal is now infed to a non-linear circuit 13, preferably a squaring circuit, at the output of which there is available a signal B (FIG. 7) having only positive signal components. At the same time the squaring insures for an improvement of the signal-to-noise ratio, since the background noises of low amplitude are amplified to a lesser degree by virtue of the squaring characterisitic of the non-linear circuit 13 than the useful signals of high amplitude. The thus formed output signal of the circuit 13 is delivered both to a trigger circuit 14 and a control circuit or regulator 15. The control or regulator circuit 15 insures that the gain of the pre-stage or pre-amplifier 11 is adjusted such that in each case the maximum peak amplitude of the second cardiac sound $S_2$ corresponds to a predetermined voltage value. To insure that the previously occurring first cardiac sound $S_1$ does not influence the signal processing, it is filtered out by means of the control stage 5. Due to the trigger stage 14 of the heart sound part 10 there is derived a pulse-shaped signal C (FIG. 7) which characterizes the occurrence of the second heart sound $S_2$. The trigger peak of this stage 14 preferably is at about 12 percent of the peak value of the second heart sound signal $S_2$ (FIG. 7, curve B).

Figure 8:
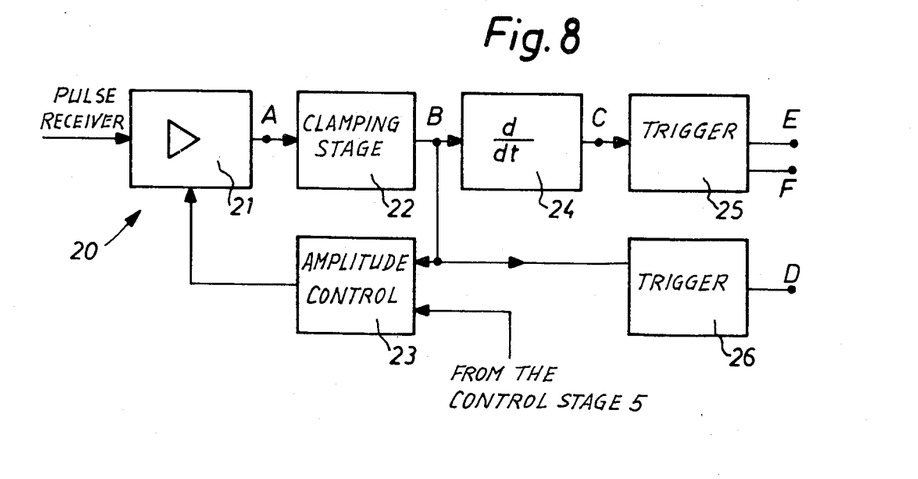
FIG. 8 is a block circuit diagram used for processing pulse pressure or pulse pressure signals.
Figure 9:
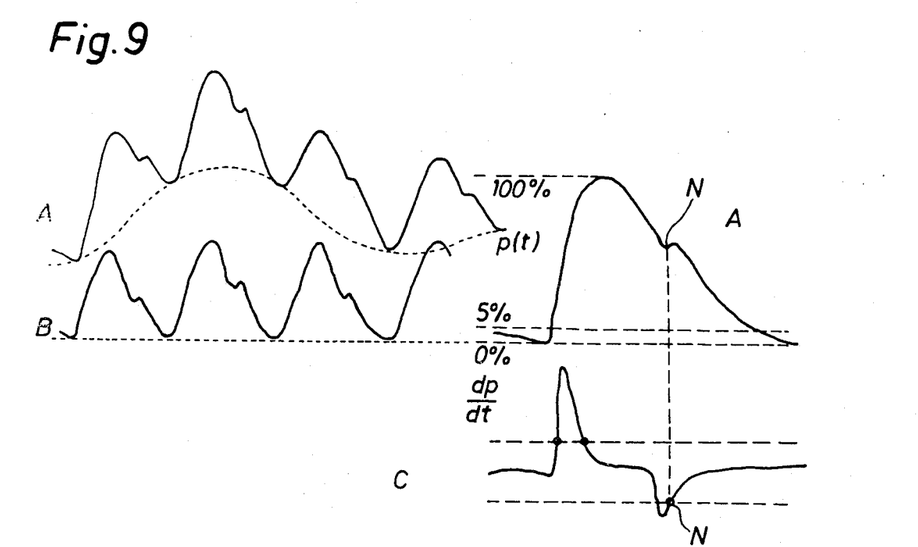
FIGS. 9 and 10 are respective graphs illustrating the shape of the signals which appear at the individual blocks of the circuit of FIG. 8.

Now the part or means 20 (FIG. 11) of the present apparatus which is intended for the analogue processing of the pulse pressure signal has been illustrated in FIG. 8 and possesses the following stages. A pre-amplifier 21 having electronically regulatable or controllable gain and which is operatively connected with a conventional and therefore not particularly shown pulse pick-up or transducer. The pulse pressure signal A (FIG. 9) which is available at the output of the pre-amplifier stage 21 has superimposed thereon an irregular low-frequency signal component which generally depends upon the movements and the breathing of the patient. These low-frequency signal components can reach extremely high amplitudes and can render evaluation of a pulse pressure curve impossible if there are not undertaken suitable measures. It is for this reason that the pulse pressure signal A, prior to further processing, is infed to a clamping stage 22 which, during each pulse beat, shifts the lowest minimum of the pulse pressure curve to the null line. Thus, each slope ascent of the pulse curve B (FIG. 9) starts from the null line or axis. The thus formed signal B is infed to a regulator or control circuit 23 which is controlled by the control stage 5 from the ECG-part 9 (FIG. 11) in such a manner that during a short period at the time of occurrence of the second heart or cardiac sound there is accomplished the regulation of the gain of the pre-amplifier 21 such that the maximum amplitude of the pulse curve corresponds to a predetermined value.

At the same time the output signal B is delivered from the clamping stage 22 to a trigger stage 26 which derives a pulse-shaped trigger signal D (FIG. 10) at preferably about 5 percent of the maximum amplitude of the pulse pressure curve A. The start of this pulse-shaped signal D indicates the slope ascent of the pulse pressure curve A (in FIG. 10), in other words the start of the ejection time or LVET.

Figure 10:
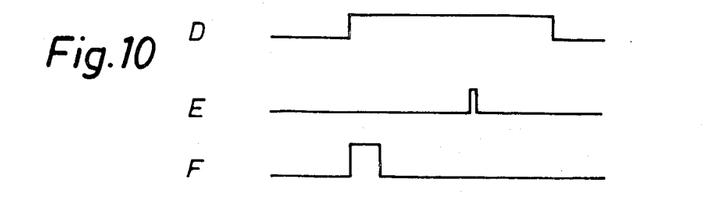

The output signal of the clamping stage 22 is infed to a differential stage 24 for forming the first time differential quotient of the pulse pressure curve A (FIG. 10). The shape of the first time differential quotient C (FIG. 10) clearly shows two peaks of opposite polarity. The first peak corresponds to the slope ascent of the pulse curve A. The second peak corresponds to the descent or drop of the pulse curve A after reaching the maximum and also the dicrotic depression N. There has been empirically determined that with the given selection of the circuit parameter, the dicrotic depression or deflection N coincides with a point of the ascending flank of the negative portion of the curve C of the first time differential quotient which approximately amounts to about 75 percent of the peak amplitude of the second peak. Hence there is characterized the occurrence of the dicrotic depression or deflection N and thus also the end of the ejection time or LVET. The recognition of the dicrotic depression N by means of the differentiating stage 24 causes a trigger circuit 25 which is connected at the output of the differentiating stage 24 to deliver a narrow pulse E (FIG. 10).

Furthermore, the trigger stage 25 derives from the first peak of the first time differential quotient the pulse-shaped signal F.

The logical AND-compounding or linking of the signals D and F indicates the slope ascent of the pulse pressure curve A (in FIG. 10), in other words the start of the ejection time or LVET.

Figure 11:
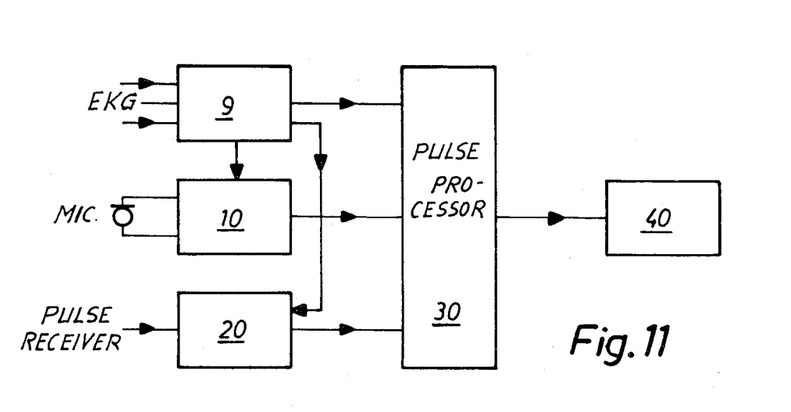
FIG. 11 is a block circuit diagram of the entire apparatus useful for the practice of the method of the present invention.

The processing of the pulse-shaped signals obtained by means of the previously described analogue processing in the system parts or components 9, 10 and 20 of the apparatus of the present invention, can be accomplished by means of fixedly wired hardware, such as the pulse processor or a computer or microprocessor 30 (FIG. 11). This component 30 of the apparatus of the present development operates in the following manner:

Upon each occurrence of the PRT-signal or the Q-signal in the ECG there is attempted to start an analysis of a heart beat. In order to eliminate disturbances and the P-waves of the ECG the R-signal must follow within a certain time. If owing to two small Q-waves of the ECG this cannot be detected, then the analysis is started upon the occurrence of the R-signal and at the end of the analysis there is added in the processor or computer 30 an empirically determined correction time which corresponds to the time spacing between the Q-signal and the R-signal. If one of the time correlations is not within the predetermined tolerances, then the pulse beat is distorted and the analysis is again started at the next pulse beat.

By means of the R-pulse (FIG. 5) there is furthermore triggered the duration of a time signal which preferably is dependent upon the pulse frequency, during which there has occurred the first heart sound $S_1$, which thus has been filtered out or eliminated. Furthermore, there is derived from the R-pulse a time window which starts after a certain time $t_1$ following the occurrence of the R-signal or trigger and ends after a time $t_2$. Within this time window there must be accomplished the triggering of the ascent or rise of the pulse pressure curve A (FIG. 10). The time limits $t_1$ and $t_2$ are stretched quite wide at the start and after about eight pulse beats this window is intensely narrowed in accordance with the mean of the preceding four beats.

After expiration of the first frequency-dependent time or timing signal for cutting-out the first heart sound $S_1$ there is waited for the pulse C (FIG. 7) in accordance with the second heart or cardiac sound $S_2$. If the signal B (FIG. 7) at the output of the squaring stage 13 contains more than 50 percent positive signal components, then it is accepted as the heart sound signal and with the start thereof there is terminated the evaluation period which extends from the Q-wave of the ECG up to the start of the second heart or cardiac sound $S_2$. As a result there has been established the electro-mechanical systole.

A further time window, preferably lasting from 2 to 40 milliseconds after the occurrence of the second cardiac sound $S_2$, serves for controlling the temporal correctness of the dicrotic depression N of the pulse pressure curve which defines the end of the ejection phase or LVET.

If for a pulse beat complex there should be fulfilled the timewise or temporal correlation at all three signals and all three trigger points can be faultlessly detected, then there is checked whether the delivered timing or time signals for the electro-mechanical systole $QS_2$ and the ejection phase or LVET are located within the thresholds or boundaries dependent upon the pulse frequency. If this is the case then the result is finally accepted as being representative.

In the same manner there is now determined the result of twelve pulse beats and the momentary result is stored. Consequently, the results of those two pulse beats are eliminated whose individual measuring values deviate most from the formed mean values. From the remaining ten pulse beats there is then formed the mean values. From the formed mean values for the duration of the electro-mechanical systole $QS_2$ and for the ejection time or LVET there is formed a difference which constitutes the contraction time or PEP. Further there is also indicated the pulse frequency which is determined from the ten time intervals between the successive R-waves of the ECG.

The present apparatus is also designed in such a manner that disturbances in the primary signals which are tapped-off the patients are automatically detected and eliminated. For this purpose there are checked the timewise correlation of the characteristic points of the signals which are determinative of the systolic time intervals. These characteristic points are located in relation to one another in a certain temporal or timewise correlation, the variation range of which can be empirically determined and fixed as a function of the pulse frequency. For checking the temporal correlation of the individual signals with respect to one another there can be used, apart from the above-described characteristic moments of the signals, also auxiliary or supplementary moments. These are the total duration of a pulse period, measured as the spacing between two R-waves of the ECG and a signal derived from the ECG which documents the presence of the P, R, T-wave of the ECG. If there is detected from one of the introduced criteria of the temporal correlation a fault in a signal, then the result of the signal evaluation is suppressed for the relevant pulse duration or period and is not incorporated into the detection.

According to a preferred embodiment of the apparatus of the invention there is also contemplated a mode of operation for the continuous evaluation of the systolic time intervals. In this operational mode there is likewise considered in each case twelve pulse beats which are recognized as artifact-free. From one such group of twelve pulses there is undertaken, analogous to the above-described technique, the evaluation of the systolic time intervals and there is indicated their mean value. The next group of pulse beats which are employed for determining and forming an individual result, is shifted further in time in relation to the preceding group by four pulse beats. As a result there is realized a sliding meaning process wherein two successive periods conjointly contain eight pulse beats, and in each case there are newly incorporated four pulse beats, however there are eliminated instead four pulse beats of the preceding period from the analysis. Furthermore, this periodic method is characterized by the features that the tolerance limits for the checking of the correctness of the timewise correlation is always adjusted from the mean or average of a group of four pulse beats which have been determined to be correct. As a result there is realized an extensive adaptation of the checking or testing crieria to the actual conditions and there is realized an appreciably exacter selection of possible disturbances.

In the preferred embodiments of the present apparatus the analogue signals for the ECG, heart sound and pulse pressure curves as well as the results from the processor section or pre-processor 30 indicated in numerical form are visibly displayed at an indicator or display device 40 having an imaging screen or equivalent structure.

Finally, there are here still underscored a number of appreciable aspects of the present method as well as the present apparatus, and there also will be indicated a number of advantages which can be realized with such method and the apparatus for the performance thereof. As will be apparent from the previous explanations there are formed two intervals. The first time interval extends from the start of the Q-wave in the ECG-signal up to the start of the second heart sound $S_2$. This constitutes the total duration of the electro-mechanical systole $QS_2$. The second time interval begins with the slope ascent of the pulse pressure curve A (FIG. 10) and terminates with the dicrotic depression N. This time interval constitutes the ejection time or LVET. From the total duration of the electro-mechanical systole $QS_2$ and the ejection time or LVET there is determined the contraction time or $PEP=QS_2-LVET$. Thus there can be computed the contraction time or PEP and equally the previously discussed quotient which is formed from the contraction time or PEP and the ejection time or LVET.

This determination or detection process should be performed at a number of, preferably successive pulse beats. As stated, there are preferably evaluated ten pulse beats and there is formed the mean value of the systolic time intervals $QS_2$. The signals which are derived from the patient by means of the preamplifiers 1, 11 and 21, must be standardized with regard to their maximum amplitude and their null position. Thus for each heart beat there is placed into operation the regulator circuits 4, 15 and 23 during a short period of time, and which regulate the maximum deflection of the ECG-signal, the second heart sound $S_2$ and the pulse pressure curve A to a predetermined level.

The ECG-signals are also standardized as concerns their frequency band width by means of the frequency-dependent elements, i.e., filters. In particular, there are thus eliminated the extremely low-frequency fluctuations which are oftentimes superimposed upon such signals, these fluctuations being brought about by breathing movements. There thus are produced ECG-signals, wherein the isoelectrical line in the electrocardiogram coincides with the null potential of the entire electronic apparatus. The heart sound signals are only received at a certain predetermined frequency band width, so that spurious signals or noise and ambient noise are extensively suppressed. Finally, the aforementioned transformation of the pulse pressure curve is accomplished such that the lowest point of the signal course B (FIG. 9), shortly prior to the start of the slope ascent of the curve A, always comes to lie exactly at the electronic null line.

While there are shown and described present preferred embodiments of the invention, it is to be distinctly understood that the invention is not limitied thereto, but may be otherwise variously embodied and practiced within the scope of the following claims. Accordingly,

What is claimed is:

1. An apparatus for determining systolic time intervals from an electrocardiogram, the heart sound and the pluse pressure curve of a patient, comprising:
   analogue signal processing means for electrocardiogram signals;
   analogue signal processing means for heart sound signals;
   analogue signal processing means for pulse pressure signals; and
   process control means containing a computer means and display device;
   each analogue signal processing means having a respective output connected to said computer means;
   said analogue processing means for electrocardiogram signals having a second output connected to an amplitude and trigger control input of said analogue signal processing means for heart sound signals and having a third output connected to an amplitude control input of said analogue signal processing means for pulse pressure signals.

2. The apparatus as defined in claim 1, wherein:
   said analogue signal processing means for the electrocardiogram signals comprises an amplifier;
   said amplifier having an input which can be connected by means of electrodes with a patient;
   said amplifier having an output;
   a signal separator;
   a clamping circuit having an input and output and connecting the output of the amplifier with the signal separator;
   said signal separator having a positive output;
   a control stage and two trigger stages;
   the positive output of the signal separator being connected with the control stage and the two trigger stages;
   regulator means connected with the output of the clamping circuit;
   the control stage controlling by means of the regulator means the amplifier;
   a third trigger stage;
   the signal separator having a negative output connected with said third trigger stage;

one of said two trigger stages having an output connected with the clamping circuit.

3. The apparatus as defined in claim 1, wherein:

said analogue signal processing means for heart sound signals comprises:

a pre-amplifier having an output;

a non-linear circuit having an output;

a bandpass connecting the output of the preamplifier with the non-linear circuit;

a trigger circuit and an amplitude-regulation circuit;

the output of the non-linear circuit being connected with the trigger circuit and the amplitude regulation circuit;

a control stage controlling the trigger circuit and the amplitude-regulating circuit;

the output of the amplitude-regulating circuit regulating the gain of the pre-amplifier.

4. The apparatus as defined in claim 1, wherein:

the analogue signal processing means for the pulse pressure signals comprises:

a pre-amplifier having an output;

a clamping stage having an input and an output;

the output of the pre-amplifier being connected with the input of the clamping stage;

a first trigger circuit and a second trigger circuit;

a differentiation stage for connecting the output of the clamping stage with the first trigger circuit;

the output of said clamping stage being further connected with said second trigger circuit;

a regulation stage;

the output of the clamping stage controlling the regulation stage;

a control stage for controlling said regulation stage; and the regulation stage having an output which controls the pre-amplifier.

5. The apparatus as defined in claim 1, wherein:

the respective means for analogue signal processing of the electrocardiogram signals, heart sound signals and pulse pressure signals each have a respective output side connected with the computer means of the process control means;

the computer means having an output; and the output of the computer means being connected with said display device.

* * * * *